United States Patent
Koenig (10) Patent No.: US 11,918,707 B2
(45) Date of Patent: *Mar. 5, 2024

(54) IMPLANT, PREFERABLY FOR THE TREATMENT OF AN ACETABULAR DEFECT

(71) Applicant: Aesculap AG, Tuttlingen (DE)

(72) Inventor: Silke Koenig, Rottweil (DE)

(73) Assignee: AESCULAP AG, Tuttlingen (DE)

( * ) Notice: Subject to any disclaimer, the term of this patent is extended or adjusted under 35 U.S.C. 154(b) by 146 days.

This patent is subject to a terminal disclaimer.

(21) Appl. No.: 17/369,319

(22) Filed: Jul. 7, 2021

(65) Prior Publication Data

US 2021/0338903 A1 Nov. 4, 2021

Related U.S. Application Data (63) Continuation of application No. 16/323,078, filed as application No. PCT/EP2017/069376 on Aug. 1, 2017, now Pat. No. 11,110,208.

(30) Foreign Application Priority Data

Aug. 2, 2016 (DE) ...................... 10 2016 214 258.5

(51) Int. Cl.
| | | |
|---|---|---|
| A61L 27/58 | (2006.01) | |
| A61F 2/30 | (2006.01) | |
| A61L 27/04 | (2006.01) | |
| A61L 27/18 | (2006.01) | |
| A61L 27/24 | (2006.01) | |
| A61L 27/36 | (2006.01) | |

(Continued)

(52) U.S. Cl.
CPC .............. *A61L 27/58* (2013.01); *A61L 27/047* (2013.01); *A61L 27/18* (2013.01); *A61L 27/24* (2013.01); *A61L 27/3604* (2013.01); *A61L 27/3625* (2013.01); *A61L 27/54* (2013.01); *A61L 27/56* (2013.01); *A61L 2300/406* (2013.01); *A61L 2430/02* (2013.01); *A61L 2430/24* (2013.01)

(58) Field of Classification Search
CPC ........ A61L 27/58; A61L 27/047; A61L 27/18; A61L 27/24; A61L 27/3625; A61L 27/54; A61L 27/56; A61L 2300/406; A61L 2430/02; A61F 2/30756
See application file for complete search history.

(56) References Cited

U.S. PATENT DOCUMENTS 6,843,807 B1    1/2005  Boyce
9,439,764 B2 *  9/2016  Shim ......................... A61F 2/28
(Continued)

FOREIGN PATENT DOCUMENTS

DE    102005018644    11/2005
EP         2428233    10/2015
(Continued)

*Primary Examiner* — Bruce E Snow
(74) *Attorney, Agent, or Firm* — Lewis Kohn & Walker LLP; David M. Kohn (57) ABSTRACT

An implant, preferably for treating and/or reconstructing, in particular lining and/or sealing and/or relining and/or at least partially filling an acetabular defect, having at least one flat structure which contains a material that is at least partially decomposable or resorbable in vivo. The invention further relates to a surgical kit and the use of an unfinished flat structure for producing an implant.

20 Claims, 5 Drawing Sheets

(51) Int. Cl.
*A61L 27/54* (2006.01)
*A61L 27/56* (2006.01)

(56) References Cited

U.S. PATENT DOCUMENTS

| | | | |
|---|---|---|---|
| 11,110,208 B2* | 9/2021 | Koenig | ............... A61L 27/3625 |
| 2002/0035401 A1 | 3/2002 | Boyce | |
| 2017/0119933 A1 | 5/2017 | McKay | |

FOREIGN PATENT DOCUMENTS

| | | |
|---|---|---|
| WO | 2010093333 | 8/2010 |
| WO | 2013077896 | 5/2013 |
| WO | 2015162559 | 10/2015 |

* cited by examiner

IMPLANT, PREFERABLY FOR THE TREATMENT OF AN ACETABULAR DEFECT

The invention relates to an implant, preferably for treating an acetabular defect, a surgical kit comprising such an implant, and use of at least one unfinished flat structure for producing such an implant.

The increasing number of revision and replacement operations after implantation of total hip endoprostheses is one of the greatest challenges in modern therapeutic surgery. What has been found to be particularly problematic in this context is the loss of bone tissue from the acetabulum and femur that generally accompanies revisions.

The restoration of anatomical bone conditions, in particular a biomechanically correct position of the implant, is therefore of particular importance.

In general, there are various therapeutic options available.

For example, bone defects of the acetabulum can be reconstructed by means of large cement-free cups, revision rings, supporting shells, or ceramic transplants, or alternatively be bridged over by means of modular porous metal augmentation.

Larger bone defects of the acetabulum must first be filled prior to implantation of an endoprosthesis in the context of both primary care and revision. In bone defects of Paprosky classification 2C (isolated medial cup migration, intact acetabular rim) and 3A (significant superolateral cup migration >3 cm; 40-60% contact with the implant bed; insufficient stability; risk of pelvic discontinuity), filling is carried out as a rule using bone chips.

In the case of revision surgery, autologous hip bone is ordinarily not available, and for this reason one must resort to allogeneic bone grafts.

For this purpose, one uses either bone chips produced from the femoral head during surgery or structural allogeneic transplants, e.g. femoral head augmentation.

The objective is to produce a bone bed that allows mechanically secure implantation of a socket. Reconstruction by bone transplantation is indispensable in particular in the case of advanced, combined structural defects with bone volume loss. This is a technically complex surgical procedure that requires a correspondingly experienced and seasoned surgeon. Otherwise, failure of the implanted endoprosthesis is inevitable.

In the case of bone chips, the chips are inserted into the defect cavity in layered fashion and impacted. Impacting of the bone chips is often carried out using a so-called impactor (a surgical instrument for impacting bone chips or bone shavings). It is important to achieve favorable interlocking of the bone chips among one another and with the remaining bone tissue. Particularly suitable are the bone chips referred to as "fresh-frozen grafts".

In order to produce such bone chips, a femoral head stored at −80° C. is first cut into slices using a saw. The spongiosa is then thoroughly washed to remove any residual fat or blood. The smooth cartilage is then completely removed, as this can prevent trabeculae from growing through.

The bone chips are then prepared—if possible using a Luer bone rongeur (a straight, transmission-free cutting device having gouging-type jaws for removing bone edges and cartilage) or in comparable sizes.

However, almost all bone mills produce "bone meal", which does not have sufficient mechanical stability. The ideal size of bone chips is 0.7 cm to 1.0 cm. In production using bone mills, however, it is only possible to achieve chip sizes of about 2 mm to 6 mm. The maximum stability is achieved using spongious bone chips in a wide variety of sizes within the range of 0.7 cm to 1.0 cm.

Before insertion, the remaining natural bone bed must be carefully milled or drilled in order to obtain a vital support for the bone chips. After insertion, the bone chips must be compressed to the maximum degree ("impaction grafting"). A prerequisite for this is the presence of a corresponding boundary formed by still-present bony defect walls.

Incorporation of the bone chips is carried out by means of endochondral ossification (bone formation from the inside) along the osteoconductive border (the scaffold for natural bone growth) of the chips, wherein mechanical stability will increase over the course of time.

After augmentation of the natural bone with bone chips, both cemented and cement-free cups can be used.

In the case of larger defects, in order to keep the bone chips in place and obtain a counter-bed for impacting, so-called revision meshes are often inserted into the bone defect. This eliminates the risk that the compacted bone chips will be pressed through the defect and thus damage bone tissue.

The revision meshes are anatomically formed so that they can be directly used for the revision surgery or, if necessary, can be adapted by bending. In addition, the meshes can be provided with preconfigured holes that allow fixation with screws.

The revision meshes are composed of non-decomposable metal. There is therefore a risk that the metal meshes will grow together with the bone chips and the bone. If a revision is required and removal of the metal mesh is necessary for surgical reasons, fresh bone is also constantly removed, which means that the defect will become larger and also that bone neoformation can be impaired. In addition, metal residues remaining in the bone defect may interfere with the surgical procedure and adversely effect the therapeutic outcome.

The object of the present invention is therefore to provide an alternative implant to the revision meshes known from the prior that in particular overcomes the above-mentioned drawbacks to the extent possible.

This object is achieved by means of an implant for use in treating, in particular lining and/or sealing and/or relining and/or at least partially filling an acetabular defect, having at least one flat structure which contains a material that is at least partially decomposable or resorbable in vivo, a surgical kit comprising an implant and at least one component selected from the group composed of bone filling material, textile mesh, bone adhesive, endoprosthesis, supporting shell, spacer implant and fastening element and use of an unfinished flat structure which contains a material that is at least partially decomposable or resorbable in vivo for producing an implant. Preferred embodiments are defined in the dependent claims. The wording of all of the claims is hereby incorporated into the content of the present description by express reference. The invention further relates to a method for treating and/or reconstructing an acetabular defect.

According to a first aspect, the invention relates to an implant, preferably for treating and/or reconstructing, in particular lining and/or sealing and/or relining and/or of at least partially filling an acetabular defect.

The implant is characterized in particular in that it comprises at least one flat structure or is composed of at least one flat structure which has a material that is at least partially decomposable (degradable) in vivo or a material that is at least partially resorbable in vivo.

By means of the material that is at least partially decomposable or resorbable in vivo, in the case of required revision or replacement operations, bone loss resulting from bone adhesions can be significantly reduced compared to generic revision meshes or even completely prevented.

The term "flat structure" is to be understood within the meaning of the present invention as preferably referring to a structure that in two of its dimensions, preferably its length and width, is considerably larger than in its third dimension, preferably its height or thickness.

The term "at least one flat structure" is to be understood within the meaning of the present invention as referring to a flat structure or a plurality of flat structures, i.e. two or more, for example two, three or four, in particular two flat structures.

The term "decomposable in vivo" or "degradable in vivo" is to be understood within the meaning of the present invention as referring to a material that is metabolized in a human or animal body, in particular under the action of enzymes. The decomposition of the material can continue all the way to mineralization, i.e. the release of chemical elements and incorporation thereof into inorganic compounds, such as e.g. carbon dioxide, oxygen and/or ammonia, or remain at the stage of decomposition-resistant intermediate or transformation products.

The term "resorbable in vivo" is to be understood within the meaning of the present invention as referring to a material that is absorbed in a human or animal body by living cells or living tissue, such as e.g. the kidneys, without the occurrence of any or any significant decomposition of the material.

The term "animal body" is to be understood within the meaning of the present invention as referring to the body of a non-human mammal, such as e.g. a horse, cow, goat, sheep, pig or a rodent such as e.g. a rabbit, rat or mouse.

The term "material" can refer within the meaning of the present invention to a material in the sense of a pure material, but also to a material mixture, i.e. a mixture of different materials.

With respect to suitable materials, reference is made to the explanations below.

In a preferred embodiment, the material is a material that is only partially decomposable in vivo or only partially resorbable in vivo. A material that is only partially decomposable in vivo or only partially resorbable in vivo is advantageous in that this facilitates the biological reconstruction of an acetabular defect.

In an alternative embodiment, the material is a material that is completely decomposable in vivo or completely resorbable in vivo. A material that is completely decomposable in vivo or completely resorbable in vivo has the advantage that it can be completely replaced by newly-formed bone tissue and after decomposition or resorption of the material, no foreign matter remains in the original defect area.

In a further embodiment, the material has a randomized fiber structure, i.e. a structure composed of randomly arranged and/or oriented fibers.

In particular, the material can have a web or nonwoven-type structure or be configured in the form of a web, in particular a nonwoven fabric.

In a further embodiment, the material is free of non-collagenous components, in particular free of non-collagenous proteins.

Preferably, the material is a biopolymer, i.e. a naturally occurring polymer.

Particularly preferably, the material, in particular the biopolymer, is a protein, in particular an extracellular protein.

The protein is preferably selected from the group composed of collagen, gelatin, elastin, reticulin, fibrin, fibronectin, laminin, albumin and mixtures of at least two of the aforementioned proteins.

In a particularly preferred embodiment, the material, in particular the protein, is a collagen, in particular collagen type I, collagen type III or a mixture of collagen type I and collagen type III.

In a further embodiment, the material is an extracellular matrix of a biological tissue. The term "biological tissue" is to be understood within the meaning of the present invention as referring in particular to an animal tissue, i.e. a tissue occurring in animals, or a tissue produced by means of tissue reconstruction technology (tissue engineering).

Preferably, the material is an extracellular matrix of an animal or xenogeneic tissue, in particular bovine, equine or porcine tissue.

In a further embodiment, the material is a biological, in particular animal or xenogeneic, preferably bovine, equine or porcine tissue. Particularly preferred is a bovine tissue.

In a further embodiment, the material is produced from a biological, in particular an animal or xenogeneic, preferably a bovine, equine or porcine tissue. Particularly preferably, the material is produced from a bovine tissue.

Preferably, the material is in particular a biological tissue, pericardium, pericardium fibrosum, pericardium serosum, epicardium or a mixture of at least two of the aforementioned materials, in particular a tissue.

According to a particularly preferred embodiment, the material, in particular the biological tissue, is pericardium, preferably bovine pericardium, i.e. pericardium from cattle.

Such a material is already commercially distributed by the applicant under the brand name Lyoplant® for dural replacement. It is a pure collagen implant produced from bovine pericardium.

The invention is based in particular on the surprising finding that collagen, preferably pericardium, is particularly well-suited as an implant material for treating an acetabular defect. As collagen or pericardium is a substance that is compatible with the body, this provides a high degree of biocompatibility. Moreover, collagen or pericardium is a biologically decomposable material or tissue by means of which neogenesis of bone tissue can be promoted, thus minimizing the size of the bone defect ("defect downsizing"). The neogenesis of bone tissue is promoted in particular by the fiber structure of collagen or pericardium. Moreover, collagen or pericardium is a processable and in particular formable material or tissue that can be adapted to the bone defect sizes and geometries of individual patients without problems. In addition, collagen or pericardium is a material or tissue that is resistant to tensile stress, so that it can also perform load-bearing functions. If a revision is necessary, any collagen or pericardium remaining in the area of the defect can be left in the body of the patient without adversely affecting the revision outcome.

In a further embodiment, the material, in particular biopolymer, is a polysaccharide, in particular a mucopolysaccharide, preferably selected from the group composed of starch, amylose, amylopectin, dextran, dextrin, cellulose, methylcellulose, ethylcellulose, hydroxymethylcellulose, hydroxyethylcellulose, hydroxypropylcellulose, carboxymethylcellulose, carboxyethylcellulose, chitin, chitosan, hyaluronic acid, dextran sulfate, heparin, heparan sulfate, chondroitin sulfate, dermatan sulfate, keratan sulfate and mixtures of at least two of the aforementioned polysaccharides.

In a further embodiment, the material is a synthetic polymer, i.e. a polymer produced artificially, for example in a chemical laboratory or a comparable facility.

The term "polymer" is to be understood within the meaning of the present invention as referring to a homo- or copolymer.

The term "copolymer" is to be understood within the meaning of the present invention as referring to a polymer composed of at least two different monomer units.

The synthetic polymer can generally be a segmented polymer or block polymer, a statistical or randomized polymer, an isotactic polymer, a syndiotactic polymer or an atactic polymer.

In a further embodiment, the synthetic polymer is a polyhydroxyalkanoate.

In particular, the synthetic polymer can be selected from the group composed of polyglycolide, polylactide, poly-ε-caprolactone, polytrimethylene carbonate, poly-p-dioxanone (poly-1,4-dioxan-2-one), poly-3-hydroxybutyrate, poly-4-hydroxybutyrate, copolymers of at least two of the aforementioned polymers and blends of at least two of the aforementioned polymers.

In a further embodiment, the at least one flat structure, in particular the material, is in lyophilized, i.e. freeze-dried form.

In a further embodiment, the material is a metal, in particular tantalum.

In a further embodiment, the at least one flat structure comprises any desired combination or mixture of the materials described in the above embodiments.

In a further embodiment, the material has a content of 10 wt % to 95 wt %, in particular 15 wt % to 90 wt %, and preferably 20 wt % to 80 wt %, based on the total weight of the at least one flat structure.

In a further embodiment, the at least one flat structure is composed of the material that is decomposable (degradable) in vivo or resorbable in vivo.

In general, the at least one flat structure can be at least partially, in particular completely configured as a textile. For example, the at least one flat structure can be at least partially, in particular completely, in the form of a fabric, a knitted fabric such as a spun-bonded fabric, a crocheted fabric, a braided fabric, a web, a nonwoven fabric, a mesh such as a knitted mesh, a felt or a meshed fabric.

Preferably, the at least one flat structure is a textile flat structure, in particular a woven, knitted, crocheted, braided, web-shaped, nonwoven-shaped, net-shaped, felt-shaped or meshed fabric-shaped flat structure.

According to the invention, however, the at least one flat structure should preferably be configured to be at least partially, in particular completely, non-textile. Preferably, the at least one flat structure is a non-textile fiber structure, in particular a non-textile and randomized fiber structure.

In an advantageous embodiment, the at least one flat structure is configured to be flexible, in particularly bendable. In this manner, adaptation of the at least one flat structure and thus the implant to the acetabula of individual patients is possible without major difficulties.

In a further embodiment, the at least one flat structure has a varying, i.e. a non-constant layer thickness.

The at least one flat structure can in particular have a thickness of 0.1 mm to 5 mm, in particular 0.2 mm to 3.5 mm, and preferably 0.5 mm to 3.0 mm.

In a further embodiment, the at least one flat structure has a weight per unit area of 0.1 $mg/cm^2$ to 8000 $mg/cm^2$, in particular 0.5 $mg/cm^2$ to 6000 $mg/cm^2$, and preferably 0.5 $mg/cm^2$ to 5000 $mg/cm^2$.

In a further embodiment, the material has an in vivo decomposition or resorption time of 1 month to 15 years, in particular 2 months to 10 years, and preferably 6 months to 5 years.

Preferably, the at least one flat structure has a tensile strength of 10 $N/mm^2$ to 800 $N/mm^2$, in particular 15 $N/mm^2$ to 500 $N/mm^2$, and preferably 30 $N/mm^2$ to 700 $N/mm^2$.

The term "tensile strength" is to be understood within the meaning of the present invention as referring to the maximum mechanical tensile stress that the at least one flat structure tolerates before it breaks or tears. The tensile strength can be calculated in a tensile test from the maximum tensile force reached, based on the original cross-section of the at least one flat structure. In the case of a metal material, the tensile strength of the at least one flat structure can be determined, for example, by means of tensile test standardized according to EN ISO 6892-1 or ISO 6892. In the case of a polymer material, in particular a plastic material, the tensile strength of the at least one flat structure can be determined, for example, by means of a tensile test standardized according to ISO 527 or ASTM D 638. If the material is a biological tissue, in particular pericardium, the tensile strength of the at least one flat structure can be determined, for example, by means of a tensile test standardized according to ISO 9073-3.

In a further embodiment, the at least one flat structure has at least one hole, at least one perforation or at least one slit. In this manner, the growth of new bone tissue through the at least one flat structure and thus the growth of new bone tissue in the defect area can be promoted. Furthermore, for example, this makes it possible to achieve in vivo fixation of the implant, in particular by means of bone screws or bone nails.

The term "at least one hole", "at least one perforation" or "at least one slit" can within the meaning of the present invention refer to one hole, one perforation or one slit or to a plurality of, i.e. two or more, holes, perforations or slits.

Preferably, the at least one hole, at least one perforation or at least one slit is at least one hole passing through the thickness of the at least one flat structure, at least one perforation passing through the thickness of the at least one flat structure or at least one slit passing through the thickness of the at least one flat structure.

The at least one hole can in particular be configured in the form of at least one eyelet.

Particularly preferably, the at least one flat structure has a plurality of holes, perforations or slits, in particular a plurality of holes, perforations or slits passing through the thickness of the at least one flat structure.

In a further embodiment, the at least one flat structure is configured with open pores. In particular, the at least one flat structure can have an average pore diameter of 10 μm to 5000 μm, in particular 15 μm to 4000 μm, and preferably 100 μm to 3000 μm. By means of an open-pore configuration of the at least one flat structure, the formation of new bone tissue can be additionally stimulated.

In a further embodiment, the at least one flat structure comprises a central area.

In a further embodiment, the at least one flat structure has at least one elongated functional area, i.e. one elongated functional area or a plurality of elongated functional areas.

Within the meaning of the present invention, the term "elongated functional area" or "elongated functional areas" should be understood to refer to a partial area or partial areas of the at least one flat structure that has/have a greater length compared to another partial area, in particular a central area, of the at least one flat structure.

The at least one functional area is preferably designed to fasten the at least one flat structure, in particular to bone tissue that is directly adjacent to the acetabulum or an acetabular defect. Within the meaning of the present invention, therefore, the at least one functional area can also be referred to as "at least one fastening area". Accordingly, within the meaning of the present invention, the term "at least one functional area" can refer to one fastening area or to a plurality of, i.e. two or more, fastening areas.

The at least one functional area is preferably configured to be box- or strip-shaped.

In a further embodiment, the at least one flat structure has a plurality of, in particular two, three, four, five, or six, in particular two, three, or four elongated, preferably box- or strip-shaped functional areas.

Preferably, the at least one functional area, in particular the functional areas, extends out from the central area of the at least one flat structure.

In particular, the functional areas can be arranged radially around the central area of the at least one flat structure.

As mentioned above, the functional areas are preferably configured to be strip-shaped, wherein free ends of the functional areas can be configured with or without corners.

The central area is preferably configured in the form of a circular, oval, or elliptical/cylindrical body, in particular in the form of a disc.

In a further embodiment, the central area, in particular only the central area, has a multilayer, in particular a double-layer, configuration.

In a further embodiment, the at least one functional area, in particular the functional areas, in particular only the at least one functional area or only the functional areas, has a multilayer, in particular a double-layer, configuration.

In a further embodiment, the at least one flat structure has the configuration of a triple-bladed propeller or a three-leaf clover.

In a further embodiment, the at least one flat structure is integrally formed, i.e. produced from one piece of the material.

In an alternative embodiment, the at least one flat structure has a multi-part structure, i.e. the at least one flat structure is produced from a plurality of pieces of the material or a plurality of pieces that differ from one another with respect to the material, wherein the parts of the at least one flat structure, in particular the above-mentioned central area and the above-mentioned at least one functional area, in particular the above-mentioned functional areas, are connected to one another, in particular sewn together or connected to one another in a materially locking manner, for example adhesively bonded to one another. The parts, in particular the central area and the at least one functional area, in particular the functional areas, can be configured to be the same or different. According to the invention, for example in the case of a plurality of functional areas, it can be conceivable that the central area and the functional areas are configured to be different, wherein the functional areas are configured to be the same. With respect to possible embodiments of parts of a flat structure having a multipart construction or said flat structure having a multipart construction itself, the explanations given with respect to the at least one flat structure and the following explanations of an optionally present textile mesh are incorporated herein by reference in their entirety.

In a further embodiment, the implant comprises a plurality of, and preferably two, flat structures, which in each case comprise at least one material that is at least partially decomposable (degradable) in vivo or a material that is at least partially resorbable in vivo, in particular a material that is only partially decomposable in vivo or only partially resorbable in vivo or a material that is completely decomposable in vivo or completely resorbable in vivo. The flat structures can also differ from one another with respect to the material. According to the invention, however, it is preferable if the flat structures comprise the same material. With respect to the material, the above description is incorporated herein by reference in its entirety. The materials described therein with respect to the at least one flat structure also apply to cases in which the implant comprises a plurality of flat structures.

Moreover, the flat structures can be the same or different with respect to their form or structure. For example, the flat structures can be configured in each case as textiles or be configured in each case as non-textiles. Alternatively, the implant can comprise at least one textile flat structure and at least one non-textile flat structure. The above description is therefore incorporated herein by reference in its entirety. The textile and non-textile forms and structures described therein in particular with respect to the at least one flat structure also apply in cases where the implant comprises a plurality of flat structures.

For example, the implant can comprise a flat structure of bovine pericardium, in particular freeze-dried bovine pericardium, and a net-shaped, in particular knit, flat structure, for example of polyglycolide threads or threads of a terpolymer composed of glycolide, ε-caprolactone and trimethylene carbonate units.

In a further embodiment, the flat structures are arranged one above the other.

Particularly preferably, the flat structures, preferably flat structures arranged one above the other, are connected to one another, in particular connected to one another at the edges, and preferably only at the edges. For example, the flat structures can be sewn together or connected to one another in a materially locking manner, in particular adhesively bonded to one another. For example, the flat structures can be connected to one another by means of a tissue adhesive, such as e.g. by means of a fibrin adhesive.

Particularly preferably, directly adjacent flat structures, in particular flat structures arranged directly one above the other, enclose a hollow space (cavity).

In a preferred embodiment, each flat structure has a central area and at least one elongated, in particular strip-shaped, functional area, in particular a fastening area.

According to a particularly preferred embodiment, each flat structure has a central area and a plurality of elongated, in particular strip-shaped, functional areas, in particular fastening areas. In particular, the functional areas, in particular fastening areas, can be radially arranged around the central area.

In a further embodiment, the flat structures are arranged one above the other in such a way that elongated functional areas of one flat structure are arranged offset to elongated functional areas of a flat structure arranged above or below the former.

With respect to further features and advantages of the flat structures, the descriptions given with respect to the at least one flat structure are incorporated herein by reference in their entirety. The explanations given therein also apply in cases where the implant comprises a plurality of flat structures.

In a further embodiment, the implant, in particular the at least one flat structure, further comprises an additive.

In particular, the additive can be located between two adjacent flat structures, in particular between two flat structures arranged one above the other and preferably connected to one another, in particular flat structures connected to one another at the edges.

Preferably, the additive is located between central areas, in particular only between central areas of flat structures arranged one above the other and preferably connected to one another, in particular connected to one another at the edges.

Alternatively, the additive is preferably located between elongated functional areas, in particular only between elongated functional areas, of flat structures that are arranged one above the other and preferably are connected to one another, in particular connected to one another at the edges.

The additive can have a content of 2 wt % to 95 wt %, in particular 5 wt % to 90 wt %, preferably 5 wt % to 50 wt %, based on the total weight of the implant.

In a further embodiment, the additive is in the form of particles, in particular in the form of granules. The particles preferably have at least one dimension in a size range of 50 µm to 5 mm, in particular 0.5 mm to 4 mm, preferably 1 mm to 2 mm. In particular, the dimension can be the length, the height, the thickness and/or the diameter, in particular the average diameter, of the particles.

In a further embodiment, the additive is selected from the group composed of antimicrobial, in particular antibiotic, additives, osteoconductive additives, osteoinductive additives and mixtures of at least two of the aforementioned additives.

The antimicrobial, in particular antibiotic, additive can be selected in particular from the group composed of silver, copper, zinc, chlorhexidine, triclosan, polyhexamethylene biguanide (PHMB) and mixtures of at least two of the aforementioned antimicrobial, in particular antibiotic, additives.

The osteoconductive additive can be selected in particular from the group composed of calcium sulfate, hydroxyapatite, calcium phosphate, α-tricalcium phosphate, collagen, a collagen-hydroxyapatite mixture, silicon hydroxyapatite, magnesium hydroxyapatite, bioactive glass, bone shavings or chips and mixtures of at least two of the aforementioned osteoconductive additives.

The osteoinductive additive can be selected in particular from the group composed of BMP1 (bone morphogenetic protein 1), BMP2 (bone morphogenetic protein 2), BMP3 (bone morphogenetic protein 3), BMP4 (bone morphogenetic protein 4), BMP5 (bone morphogenetic protein 5), BMP6 (bone morphogenetic protein 6), BMP7 (bone morphogenetic protein 7), BMP8A (bone morphogenetic protein 8A), BMP8B (bone morphogenetic protein 8B), BMP10 (bone morphogenetic protein 10), BMP15 (bone morphogenetic protein 15), GDF10 (growth differentiation factor 10) and mixtures of at least two of the aforementioned osteoinductive additives.

In a further embodiment, the implant further comprises a textile, in particular knit, mesh. The mesh is preferably configured to reinforce the implant.

The mesh can in particular comprise a material that is decomposable in vivo or resorbable in vivo or be composed of such a material. The material can for example be selected from the group composed of polyhydroxyalkanoate, polyglycolide, polylactide, poly-ε-caprolactone, polytrimethylene carbonate, poly-p-dioxanone (poly-1,4-dioxan-2-one), poly-3-hydroxybutyrate, poly-4-hydroxybutyrate, copolymers of at least two of the aforementioned polymers and blends of at least two of the aforementioned polymers. In particular, the material that is decomposable or resorbable in vivo can be a terpolymer, in particular a terblock polymer, which is composed of polyglycolide units, poly-ε-caprolactone units and polytrimethylene carbonate units.

Alternatively, the mesh can comprise a material that is not decomposable in vivo or a material that is not resorbable in vivo or can be composed of such a material. In particular, the material can be a polyolefin, such as e.g. polyethylene, in particular ultra-high-molecular-weight polyethylene (UHMWPE), or a polypropylene, or a polyester such as e.g. polyethylene terephthalate (PET).

In particular, the mesh can be the mesh commercially distributed by the applicant under the brand name "Optilene® Mesh" or "Optilene® Mesh Elastic". The mesh "Optilene® Mesh" is a mesh of monofilament polypropylene threads, wherein the mesh has a weight per unit area of approx. 60 g/m$^2$ and a pore size of approx. 1.5 mm. The mesh "Optilene® Mesh Elastic" is a mesh of monofilament polypropylene threads, wherein the mesh has a weight per unit area of approx. 48 g/m$^2$ and a pore size of 3.6×2.8 mm.

In a further embodiment, the implant is an implant for use in treating and/or reconstructing, in particular lining and/or sealing and/or relining and/or at least partially filling an acetabular defect.

In a further embodiment, the implant is an implant for use as a counter-bed for a bone filling material in treatment of an acetabular defect. The bone filling material can be a natural bone filling material, for example bone shavings or chips, or a synthetic, i.e. an artificial bone filling material, for example calcium sulfate, hydroxyapatite, calcium phosphate, α-tricalcium phosphate, collagen, a collagen-hydroxyapatite mixture, silicon hydroxyapatite, magnesium hydroxyapatite, bioactive glass or a mixture of at least two of the aforementioned artificial bone filling materials.

In a further embodiment, the treatment is a revision.

According to a second aspect, the invention relates to a surgical kit, preferably for treating and/or reconstructing, in particular lining and/or sealing and/or relining and/or at least partially filling an acetabular defect.

The kit comprises an implant according to a first aspect of the invention.

In addition, the kit has at least one component selected from the group composed of bone filling material, textile mesh, bone adhesive, endoprosthesis, supporting shell, spacer implant and fastening element.

In general, the bone filling material can be a natural bone filling material, for example bone shavings or chips, or a synthetic bone filling material, for example calcium sulfate, hydroxyapatite, calcium phosphate, α-tricalcium phosphate, collagen, a collagen-hydroxyapatite mixture, silicon hydroxyapatite, magnesium hydroxyapatite, bioactive glass or a mixture of at least two of the aforementioned bone filling materials.

For example, the textile mesh can be a knitted mesh, in particular of polypropylene. With respect to further features and advantages of the textile mesh, the explanations given above with respect to the first aspect of the invention are incorporated herein in their entirety. The explanations given therein with respect to the textile mesh also apply (mutatis mutandis) to the surgical kit.

For example, the bone adhesive can be a curable bone cement.

The endoprosthesis is preferably an artificial socket or an artificial socket inlay.

For example, the fastening element can be a bone screw or a medullary or bone nail.

Moreover, the fastening element can be a suture material, preferably a non-resorbable suture material, for example of polypropylene or ultra-high-molecular-weight polyethylene (UHMWPE).

With respect to further features and advantages of the surgical kit, in particular of the implant, in order to avoid repetitions, the explanations given with respect to the first aspect of the invention, which also apply (mutatis mutandis) to the surgical kit, are incorporated herein by reference in their entirety.

According to a third aspect, the invention relates to the use of an unfinished flat structure for producing an implant according to a first aspect of the invention.

The flat structure has a material that is at least partially decomposable (degradable) in vivo or a material that is at least partially resorbable in vivo.

The unfinished flat structure can for example be in the form of strip goods or piece goods.

In particular, the unfinished flat structure can have templates for the implant to be produced.

Production of the implant can take place in particular by cutting to size of the unfinished flat structure. Alternatively, individual parts can be cut from the flat structure and then connected to one another, in particular sewn or adhesively bonded to one another.

With respect to further features and advantages of the flat structure, in particular the material that is at least partially decomposable or resorbable in vivo, in order to avoid unnecessary repetitions, the explanations given with respect to the first aspect of the invention are also incorporated herein by reference in their entirety. In particular, the explanations given therein with respect to the at least one flat structure also apply (mutatis mutandis) to the unfinished flat structure according to the third aspect of the invention.

According to a fourth aspect, the invention relates to a method for treating and/or reconstructing, in particular lining and/or sealing and/or relining and/or at least partially filling an acetabular defect.

The method comprises the following step:
  placement of an implant, which has at least one flat structure, wherein the at least one flat structure comprises a material that is at least partially decomposable (degradable) in vivo or a material that is at least partially resorbable in vivo or is composed of such a material, in particular placement of an implant according to a first aspect of the invention in a defective acetabulum.

In a preferred embodiment, the method further comprises the following step:
  application of a bone filling material to the placed implant.

In a further embodiment, the method further comprises the following step:
  compacting, in particular impacting, of the applied bone filling material, in particular by means of a so-called impactor. The impactor is a surgical instrument for compacting, in particular impacting, a bone filling material.

In a further embodiment, the method further comprises the following step:
  application of a bone cement to the bone filling material, in particular the impacted bone filling material.

In a further embodiment, the method further comprises the following step:
  application of a socket to the bone filling material or the bone cement.

In a further embodiment, the method further comprises the following step:
  fastening of the socket to a surrounding bone tissue, in particular to a bone tissue that is adjacent to the acetabulum or the acetabular defect.

With respect to further features and advantages of the method, in particular of the implant, the explanations given with respect to the first aspect of the invention, which also apply (mutatis mutandis) to the treatment method, are also incorporated herein by reference in their entirety.

Further advantages and features of the invention are given in the claims, the following description of preferred embodiments by means of descriptions of the figures, and the accompanying figures. In each case, features of the invention can be implemented alone or in combination with one another. The embodiments described below are for the purpose of further explaining the invention, but it is not limited to them.

DETAILED DESCRIPTION OF THE FIGURES

Figure 1:
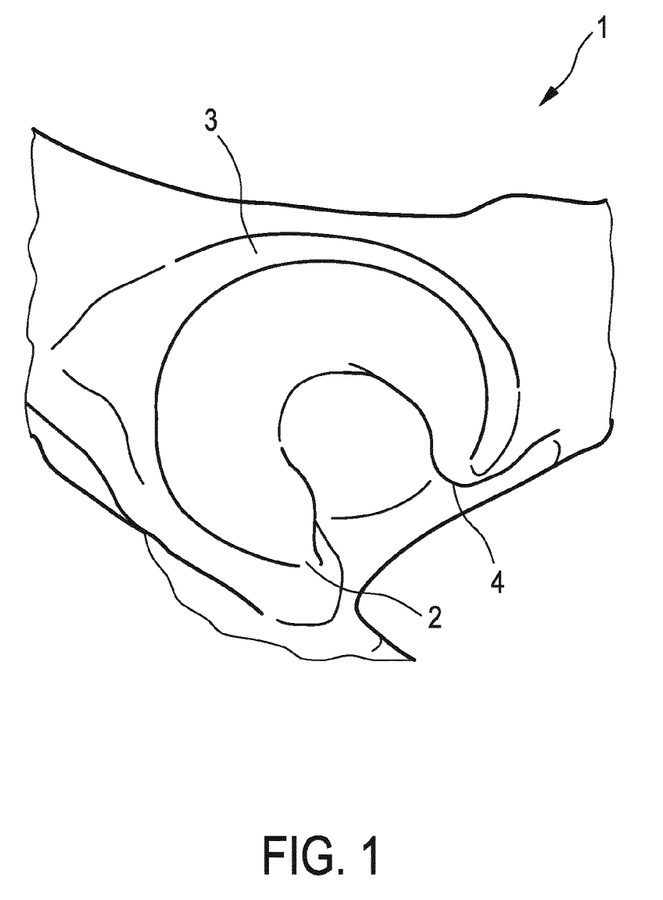
FIG. 1: a top view of a human acetabulum.

FIG. 1 shows a schematic top view of a human acetabulum 1, also referred to as the hip joint or acetabulofemoral joint. This is the bony portion of the hip joint formed by the pelvis. The acetabulum is formed by fusion of parts of the ischium, ilium, and pubic bone. This fusion is completed by the age of approx. 6 months.

Under ideal conditions, there is a conformity between the acetabulum and the femoral head, i.e. the round femoral head fits exactly into the acetabulum, which embeds and encloses it over a broad area. The hip joint is a multiaxial ball-and-socket joint and is therefore more or less freely moveable in almost every direction. This ensures a high degree of mobility and load-bearing capacity.

The joint-forming components of the hip joint are enclosed by a connective tissue capsule, whose inner lining, the synovium, constantly produces new synovial fluid. An annular articular lip of cartilage forms the edge of the bony socket.

The acetabulum 1 has an anterior acetabular rim 2, also referred to as the anterior horn, and a posterior acetabular rim 4, also referred to as the posterior horn. The cup roof 3 between these horns has a round or substantially round tapered form.

FIG. 2 shows schematic views of different embodiments of an implant according to the invention.

Figure 2A:
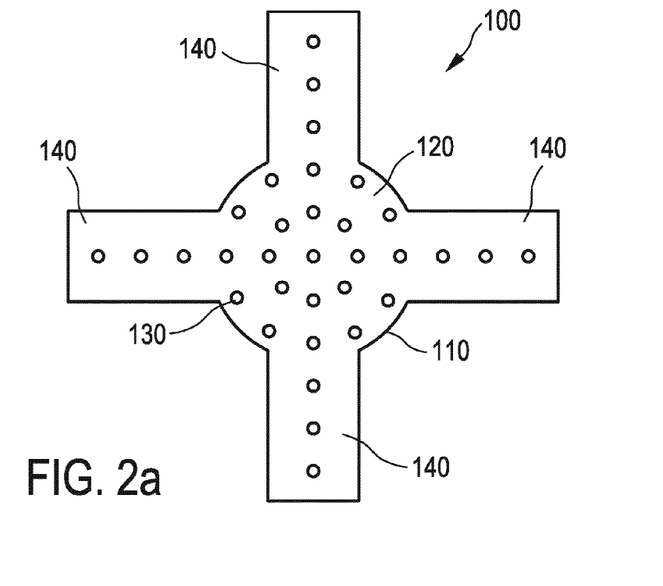
FIG. 2a-g: different embodiments of an implant according to the invention.

The implant 100 shown in FIG. 2a has a flat structure 110. The flat structure 110 has a central area 120 and four elongated functional areas 140 that extend out from the central area 120.

The central area 120 is disc-shaped.

The functional areas 140 are preferably configured to be strip-shaped. They are further preferably configured to fasten the implant 100 to bone tissue that is adjacent to an acetabulum or an acetabular defect. Within the meaning of the invention, the functional areas 140 can therefore also be referred to as fastening areas.

In order to facilitate bone growth, the implant 100 can be provided with holes 130 that preferably pass through the thickness of the flat structure 110. Here—as shown—both the central area 120 and the functional areas 140 can be provided with the holes 130. Moreover, the holes 130 can be provided for facilitated fixation of the implant 100.

Figure 2B:
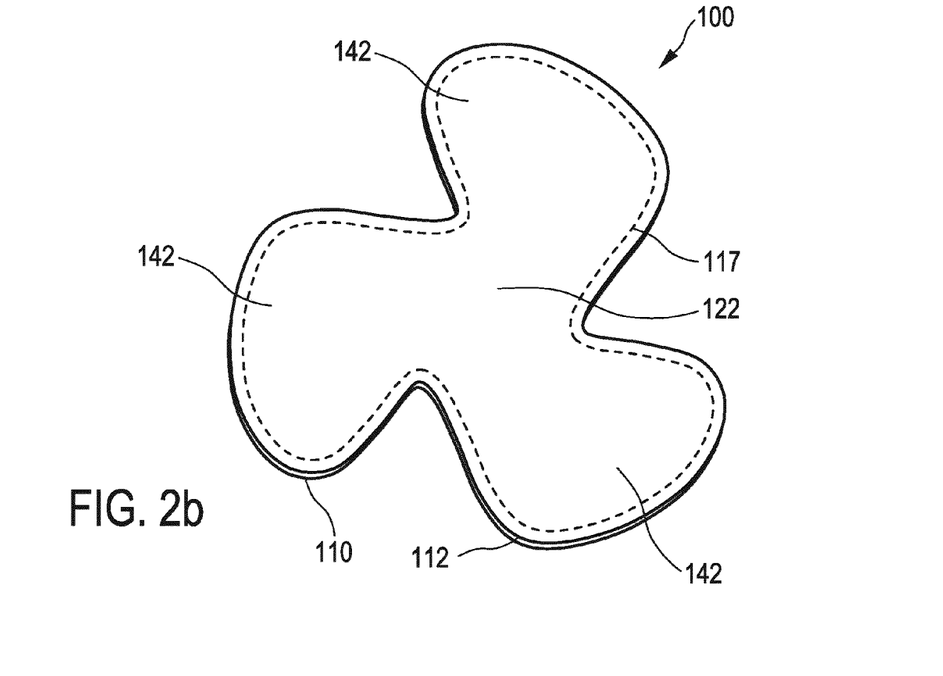

The implant 100 shown in FIG. 2b has two flat structures 110; 112 that are sewn to each other at the edges, i.e. along the edge areas of the flat structures 110; 112, by means of a suture 117. The suture 117 is preferably a suture material that is decomposable in vivo or resorbable in vivo, for example a preferably braided polyglycolide thread.

Each of the flat structures 110; 112 has a central area and three elongated functional areas that extend out from the central area. One can see in FIG. 2b the central area 122 and the three functional areas 142 of the—from the point of view of the observer—upper flat structure 112.

The implant 100 preferably has the shape of a three-leaf clover or a triple-bladed propeller.

A cavity formed between the flat structures 110; 112 can for example be at least partially filled with an osteoconductive additive and/or an osteoinductive additive. In this manner, the growth and generation of new bone tissue can be stimulated.

Figure 2C:
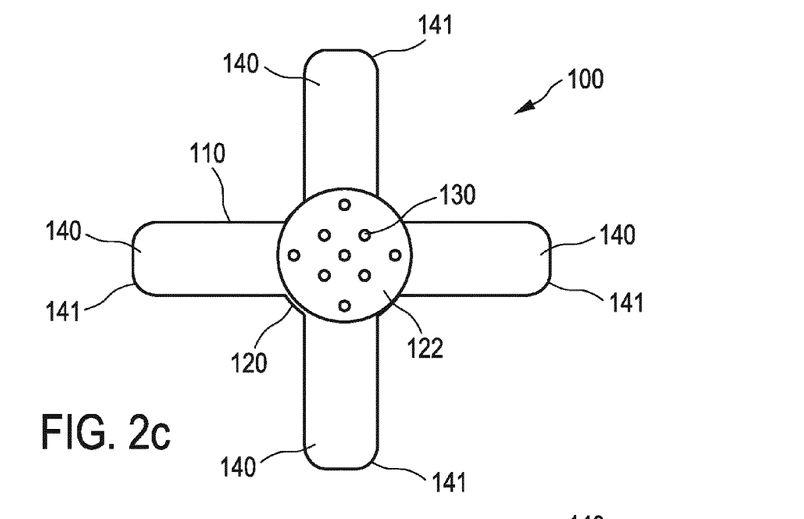

The implant 100 shown in FIG. 2c has a flat structure 110 with a central and preferably disc-shaped area 120 and four elongated, preferably strip-shaped, functional areas 140. The functional areas 140 extend out from the central area 120. The free ends 141 of the functional areas 140 are preferably configured without corners. The central area 120 is further preferably connected to a disc-shaped layer 122, in particular sewn or adhesively bonded. In order to stimulate bone growth, both the central area 120 and the layer 122 can be provided with holes 130 (that pass through the thickness of the central area 120 or the layer 122). Moreover, the holes 130 can be provided for facilitated fixation of the implant 100.

A cavity formed between the central area 120 and the layer 122 can for example be at least partially filled with an osteoconductive additive and/or an osteoinductive additive. In this manner, the growth and generation of new bone tissue can be stimulated.

Figure 2D:
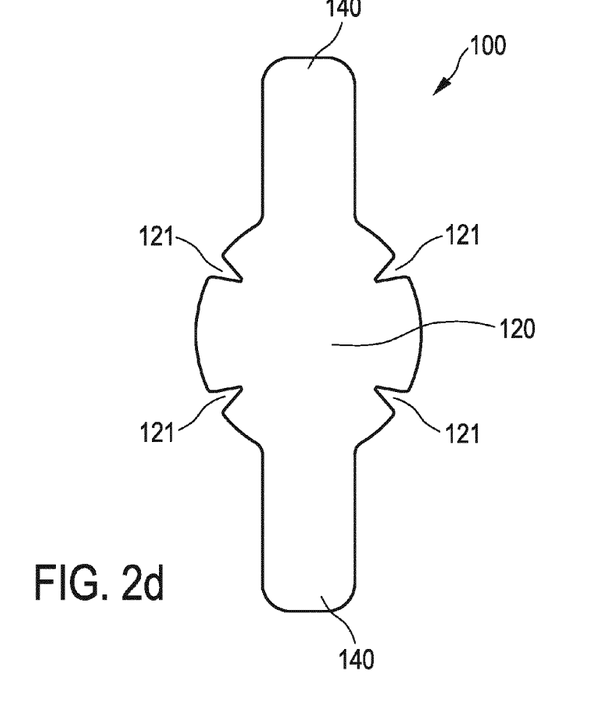

The implant 100 shown in FIG. 2d has a flat structure 110 with a central area 120 and two elongated functional areas 140 that extend out, preferably on opposite sides of the central area 120, from the central area 120. In order to facilitate adaptation to an acetabulum, the implant 100 can comprise along its central area 120 notches 121, in particular v-shaped notches.

Figure 2E:
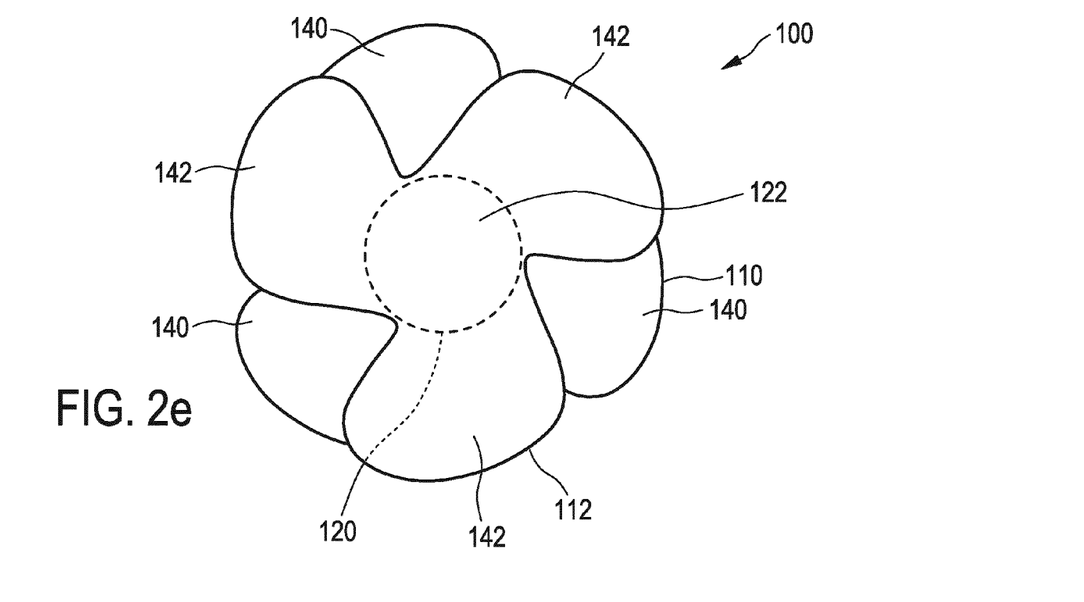

The implant 100 according to FIG. 2e has two flat structures 110; 112. Each flat structure 110: 112 has a central area 120 or 122 and three elongated functional areas 140 or 142 that extend out from the central area 120 or 122.

Each flat structure 110; 112 preferably has the configuration of a three-leaf clover or a three-bladed propeller.

The flat structures 110; 112 are preferably arranged one above the other in such a way that the functional areas 140 are arranged offset to the functional areas 142 (or vice versa).

Moreover, it is preferable for the two central areas 120, 122 to be sewn to each other at the edges. A cavity formed in this manner can for example be at least partially filled with an osteoconductive additive.

Figure 2F:
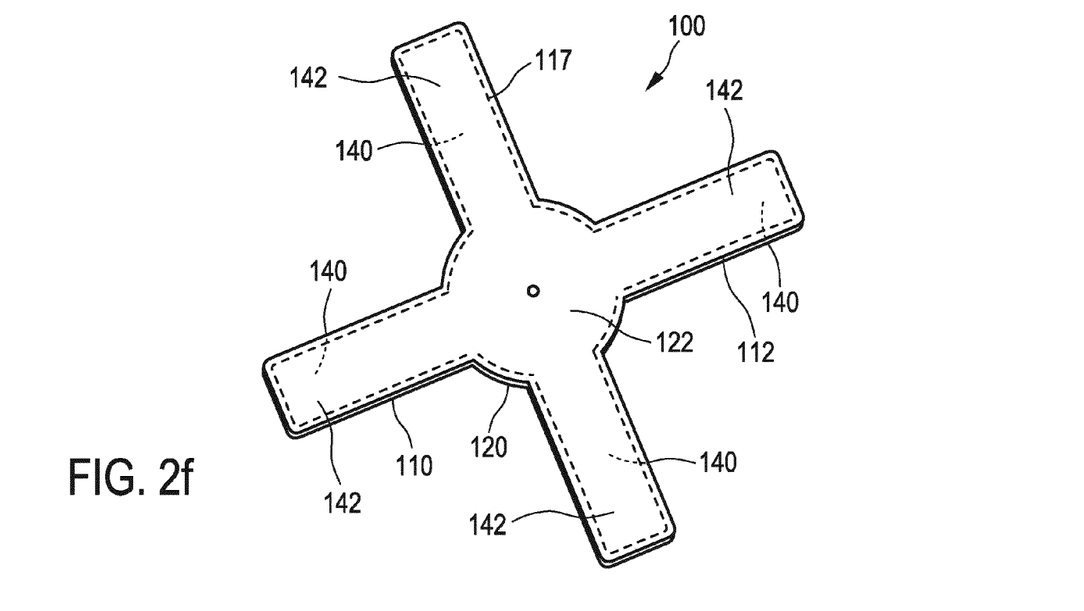

The implant shown in FIG. 2f also has two flat structures 110; 112. The flat structures 110; 112 comprise a central area 120; 122 and four elongated, preferably strip-shaped, functional areas 140; 142 that extend out from the central area 120; 122. The two flat structures 110; 112 are sewn together by means of a suture 117 along their edge areas. A cavity formed in this manner between the flat structures 110; 112 can comprise, for example for reinforcement of the implant 100, a textile mesh, in particular a knitted polypropylene mesh, for example the mesh distributed by the applicant under the brand name "Optilene® Mesh Elastic."

Figure 2G:
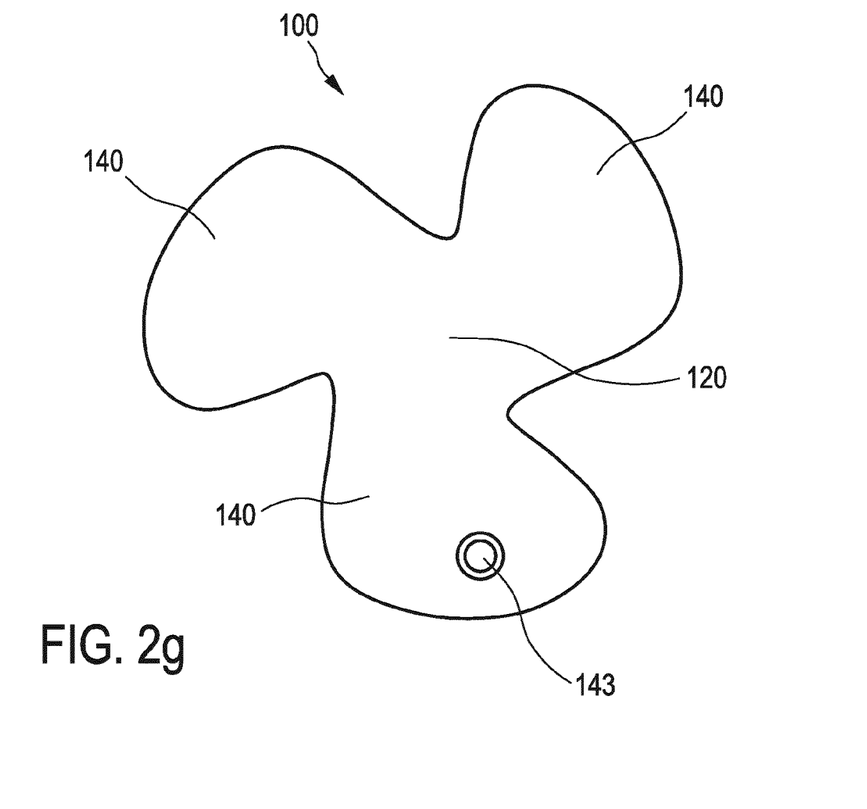

The implant 100 shown in FIG. 2g has a flat structure 110 with a central area 120 and three elongated functional areas 140. The functional areas 140 extend out from the central area 120. Overall, the flat structure 110 has a shape corresponding to that of a three-bladed propeller or a three-leaf clover. At least one of the functional areas 140 can comprise an eyelet 143 for fastening of the implant to peripheral bone tissue.

The implants shown in FIGS. 2a-g comprise a material that is at least partially decomposable in vivo or resorbable in vivo. In particular, the flat structures shown in the figures can comprise such a material completely or only partially. For example, only the central areas or only the functional areas can comprise a material that is at least partially decomposable or resorbable in vivo or be composed of such a material. The material is preferably collagen, in particular collagen type I and/or collagen type III. Particularly preferably, the material is pericardium, in particular bovine pericardium.

In addition, however, other materials are also suitable that are at least partially decomposable or resorbable in vivo. The materials disclosed in the general description are therefore incorporated herein by reference in their entirety.

The invention claimed is:

1. An implant for use in treating an acetabular defect, having at least two flat structures which are arranged directly on top of each other and attached to one another along the edge areas of each flat structure, wherein the at least two flat structures contain a material that is at least partially decomposable or resorbable in vivo, wherein the at least two flat structures comprise a central area and only three elongated functional areas, wherein the functional areas extend out from the central area of the at least two flat structures, wherein a cavity is formed in between the at least two flat structures, wherein the material has a randomized fiber structure.

2. The implant of claim 1, wherein the functional areas are arranged radially around the central area of the at least two flat structures.

3. The implant of claim 1, wherein the central area is configured in the form of a circular, oval, elliptical or cylindrical body.

4. The implant of claim 1, wherein the central area has a multi-layer configuration.

5. The implant of claim 1, wherein the functional areas have a multi-layer configuration.

6. The implant of claim 1, wherein the at least two flat structures have the configuration of a triple-bladed propeller or a three-leaf clover.

7. The implant of claim 1, wherein the at least two flat structures are a plurality of flat structures.

8. The implant of claim 1, characterized in that the material is a protein.

9. The implant of claim 8, wherein the protein is selected from the group composed of collagen, gelatin, elastin, reticulin, fibrin, fibronectin, laminin, albumin and mixtures of at least two of the aforementioned proteins.

10. The implant of claim 1, wherein the material is a synthetic polymer selected from the group consisting of polyglycolide, polylactide, poly-ε-caprolactone, polytrimethylene carbonate, poly-3-hydroxybutyrate, poly-4-hydroxybutyrate, poly-p-dioxanone, copolymers thereof and blends of at least two of the aforementioned polymers.

11. The implant of claim 1, wherein the at least two flat structures have penetrating holes, perforations or slits.

12. The implant of claim 1, wherein at least one of the functional areas comprise an eyelet.

13. The implant of claim 1, wherein the implant further comprises an additive.

14. The implant of claim 13, wherein the additive is located between the at least two flat structures that are arranged one above the other and are connected to each other.

15. The implant of claim 13, wherein the additive is located between central areas of the at least two flat structures that are arranged one above the other and are connected to each other.

16. The implant of claim 13, wherein the additive is located between functional areas of the at least two flat structures that are arranged one above the other and are connected to each other.

17. A surgical kit comprising an implant as claimed in claim 1 and at least one component selected from the group consisting of bone filling material, textile mesh, bone adhesive, endoprosthesis, supporting shell, spacer implant and fastening element.

18. An implant for use in treating an acetabular defect, having at least two flat structures which are arranged directly on top of each other and attached to one another along the edge areas of each flat structure, wherein the at least two flat structures contain a material that is at least partially decomposable or resorbable in vivo, wherein the at least two flat structures comprise a central area and only three elongated functional areas, wherein the functional areas extend out from the central area of the at least two flat structures, wherein a cavity is formed in between the at least two flat structures, wherein the material is a xenogeneic tissue.

19. The implant of claim 18, wherein the tissue is pericardium.

20. An implant for use in treating an acetabular defect, having at least two flat structures which are arranged directly on top of each other and attached to one another along the edge areas of each flat structure, wherein the at least two flat structures contain a material that is at least partially decomposable or resorbable in vivo, wherein the at least two flat structures comprise a central area and only three elongated functional areas, wherein the functional areas extend out from the central area of the at least two flat structures, wherein a cavity is formed in between the at least two flat structures, wherein the at least two flat structures are in freeze-dried form.

* * * * *